United States Patent [19]

Krull et al.

[11] Patent Number: 4,460,967

[45] Date of Patent: Jul. 17, 1984

[54] ELECTRONIC CIRCUIT FOR MEASURING AND DISPLAYING ION CONCENTRATION IN FLUID

[76] Inventors: Irwin H. Krull, 2655 Keystone #9, Santa Clara, Calif. 95051; James G. Tisue, 1074 Laureles, Los Altos, Calif. 94022

[21] Appl. No.: 283,955

[22] Filed: Jul. 16, 1981

[51] Int. Cl.³ ............................................. G01N 27/46
[52] U.S. Cl. .................................. 364/497; 364/571;
  204/1 T; 204/406
[58] Field of Search ............................. 364/497–499,
  364/571; 204/1 T, 406, 407

[56] References Cited

U.S. PATENT DOCUMENTS

| | | | |
|---|---|---|---|
| 4,028,534 | 6/1977 | Tucker | 364/497 |
| 4,043,756 | 8/1977 | Sommervold | 364/571 |
| 4,211,614 | 7/1980 | Eppstein et al. | 204/1 T |
| 4,218,746 | 8/1980 | Koshiishi | 204/406 |
| 4,321,113 | 3/1982 | Grambow et al. | 204/1 T |

*Primary Examiner*—Gary Chin
*Attorney, Agent, or Firm*—Flehr, Hohbach, Test, Albritton & Herbert

[57] ABSTRACT

The circuitry forms part of testing apparatus for measuring the concentration of ions in fluids, primarily body fluids, including the measurement of chlorides, ionized calcium, sodium and potassium as well as other ions. A small sample fluid is subjected to a controlled mechanical oscillation to thoroughly expose a true representative sample to the electrode for measurement. The apparatus has a digital readout display and two associated switches for calibrating the circuitry with high and low standard fluids. The low standard circuit is calibrated with the low standard sample to establish offset correction while the high standard circuit is calibrated with the high standard sample to establish gain correction. After the instrument has been adjusted for proper low and high standard values, for a particular electrode, the offset correction and gain correction parameters are established so that electrode input values cause proper concentrations to be displayed.

8 Claims, 6 Drawing Figures

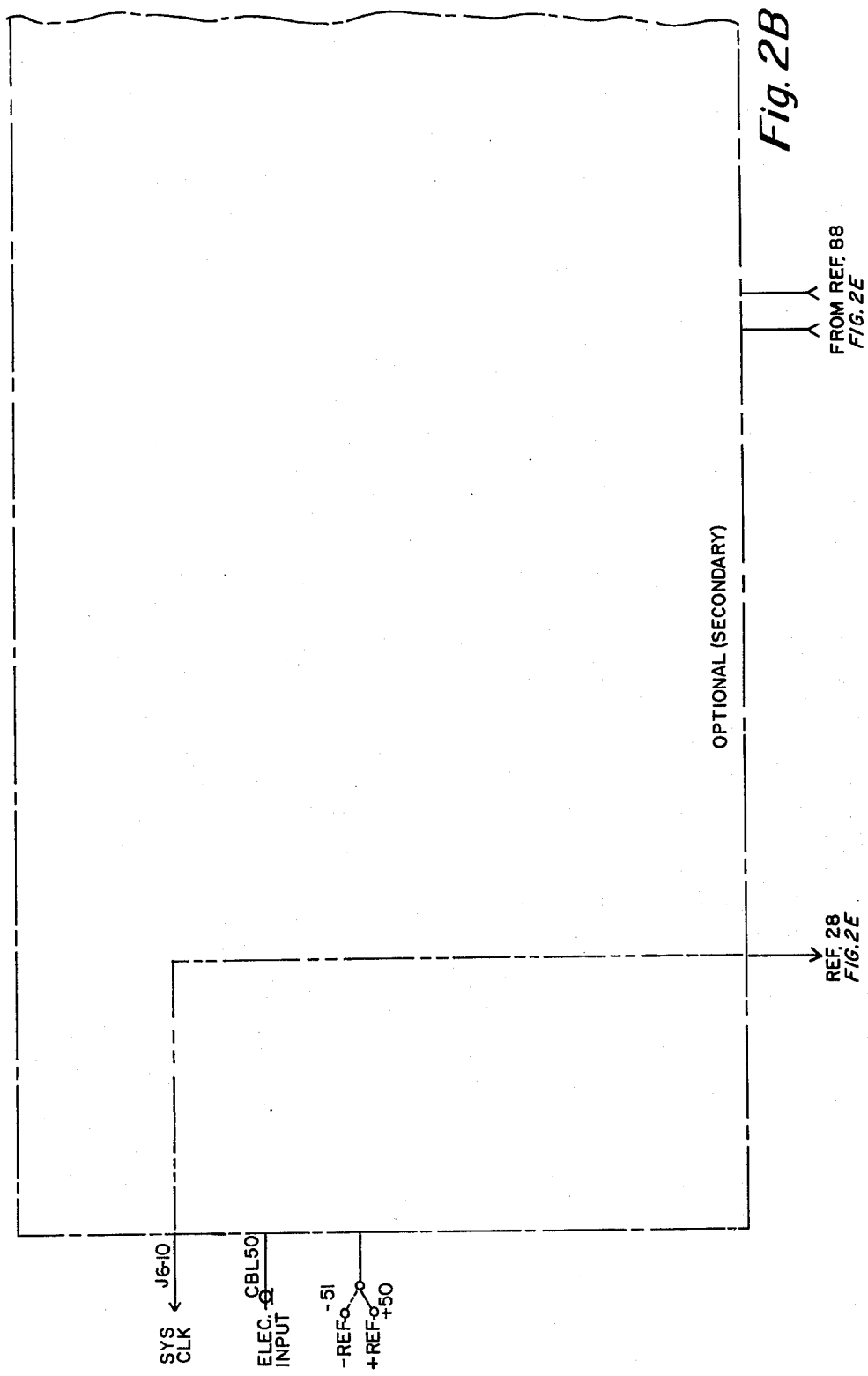

ELECTRONIC CIRCUIT FOR MEASURING AND DISPLAYING ION CONCENTRATION IN FLUID

BACKGROUND OF THE INVENTION

The present invention relates in general sense to a testing apparatus for the measurement of ions in fluids that are to be tested. More particularly, the present invention pertains to electronic circuitry for measuring and displaying the concentration of ions in body fluids including the measurement of chlorides, ionized calcium, sodium and potassium. U.S. Pat. Nos. 3,941,565; 3,994,171; and 4,048,040 describe certain prior art test methods and apparatus related to the present invention. The circuitry as described herein may be of the type used in association with the apparatus described in copending applications Ser. No. 183,983 filed Sept. 4, 1980 now U.S. Pat. No. 4,350,579.

As outlined in copending application Ser. No. 183,983, there are certain drawbacks associated with presently available testing apparatus, most of which is of the flow-through type in which the sample to be tested is moved by some means past a sensor such as an electrode partly in order that the sensor be constantly washed with the sample thereby providing a more exact measurement. These devices are generally large and may contain very intricate and complex tubing systems connected with one or more pumps to move the fluid through the tubes. The processing of signals with such apparatus is typically with the required use of a computer or microcomputer which further adds to the cost and complexity of these prior art systems.

To overcome the foregoing and other problems associated with the prior art apparatus, it is an object of the present invention to provide an electronic circuit that forms part of the testing apparatus for measuring the concentration of ions in body fluids so as to eliminate the necessity for the use of a computer in processing signals.

Another object of the present invention is to provide an electronic circuit for measuring and displaying ion concentrations in fluids wherein the circuit is a relatively simple design and capable of being integrated with the complete test apparatus.

Another object of the present invention is to provide an electronic circuit for measuring and displaying ion concentrations preferably including primary and secondary circuits with both circuits being standardized with a single control.

A further object of the present invention is to provide an electronic circuit for measuring and displaying ion concentrations employing a novel circuit combination including a counter and digital-to-analog converter in the low standard circuit and a multiplying digital-to-analog converter for slope adjustment.

Still another object of the present invention is to provide an electronic circuit for measuring and displaying ion concentrations in fluids and characterized by calibration failure indication means adapted to cause the decimal point in the display to blink to indicate such calibration errors.

SUMMARY OF THE INVENTION

To accomplish the foregoing and other objects of this invention there is provided electronic circuitry for measuring and displaying ion concentrations fluids including the measurement of chlorides, ionized calcium, sodium and potassium as well as other ions in the fluids obtained from the body or elsewhere. In the testing apparatus with which the circuitry of the present invention is employed, a small sample fluid is subjected to a controlled mechanical oscillation to thoroughly expose a true representative sample to the electrode for measurement.

The apparatus has associated therewith a digital readout display and two associated switches for calibrating the circuitry with high and low standard fluids. The low standard circuit is calibrated with the low standard sample to establish offset correction while the high standard circuit is calibrated with the high standard sample to establish gain (slope) correction. After the instrument has been adjusted for low and high standard values, for a particular electrode, the offset correction and gain correction parameters are established so that electrode input values will cause power concentrations to be displayed on the digital readout. More particularly, the electrode input to the circuitry couples to a high impedance front end amplifier or the like having an electronically adjustable reference offset. The low standard circuit includes a low standard set switch which couples to a counter adapted to be set to count from zero and stopped by means of a comparator when the buffered electrode signal is at zero or when failure occurs. This causes the output from the operational amplifier circuit to be zero at any electrode input within the electrode bias range while in the low standard sample. The output display is essentially forced to read the low standard sample value by proper adjustment of the reference voltage to the digital panel meter. After the calibration for the low standard sample, and after electrode insertion into the high standard sample, then the high standard set switch is operated. The high standard circuit includes, in addition to the set switch, a counter and a multiplying digital-to-analog converter. This converter multiplies any change in electrode input since the last low standard set operation by the value from the counter. The count operation is terminated by a comparator with its reference signal being adjusted to again require that the digital display read the high standard sample value. The output from the multiplying digital-to-analog converter couples to an anti-logarithmic device which takes into account the logarithmic relationship between electrode voltage and concentration to assure proper interpolation or extrapolation around the sample and the calibration values. There are also provided a number of calibration failure circuits which operate under certain predetermined conditions and cause the decimal point to blink to indicate such calibration failure. There is also provided an inverter that may be inserted into the circuit for use with electrodes with negative slopes.

BRIEF DESCRIPTION OF THE DRAWINGS

Numerous other objects, features, and advantages of the invention should now become apparent upon a reading of the following detailed description taken in conjunction with the accompanying drawings, in which:

FIGS. 2A–2E show schematic diagram details of the block diagram of FIG. 1.

DETAILED DESCRIPTION

Figure 1:
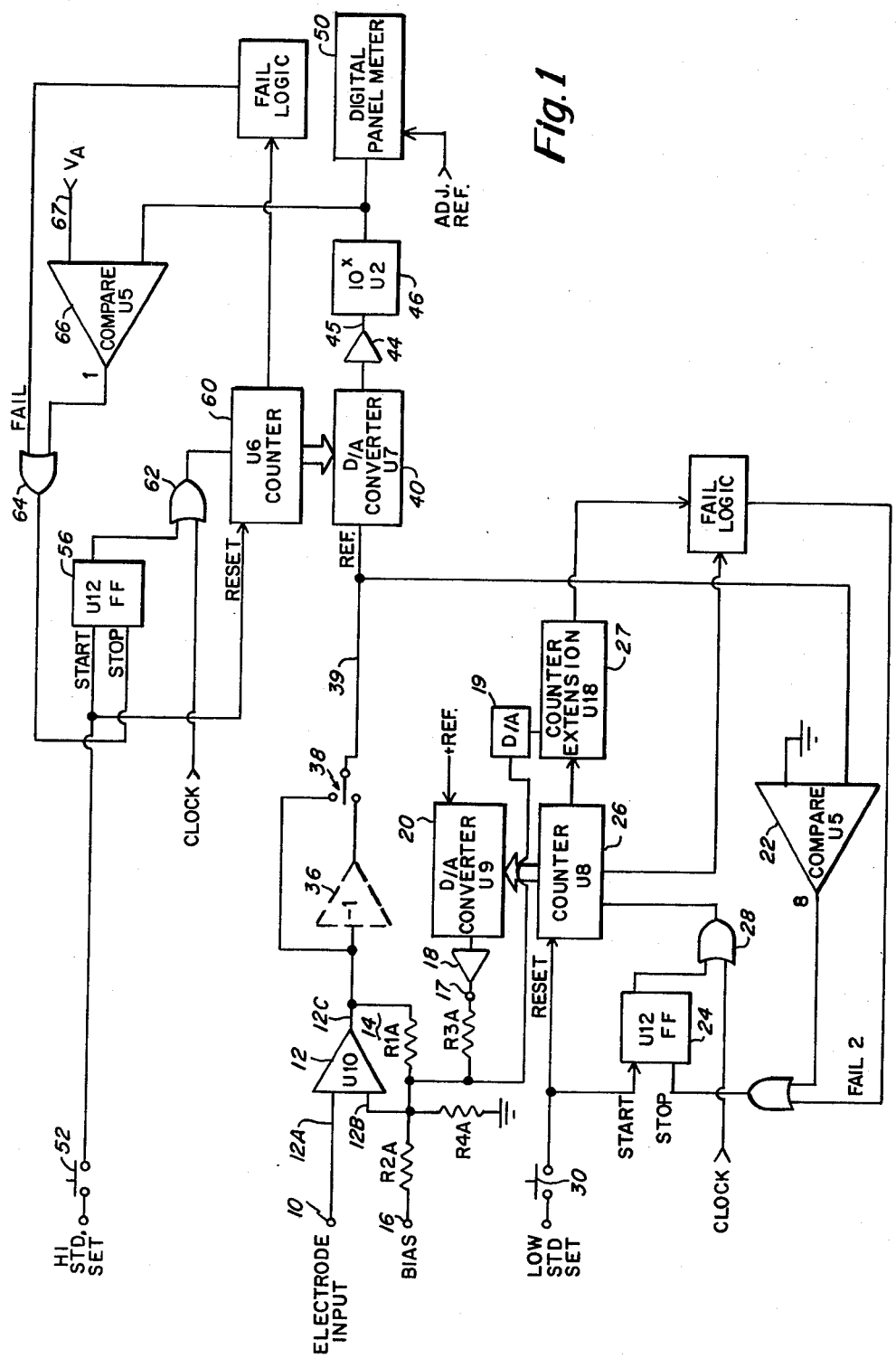
FIG. 1 is a block diagram of the system of the present invention.
Figure 2A:
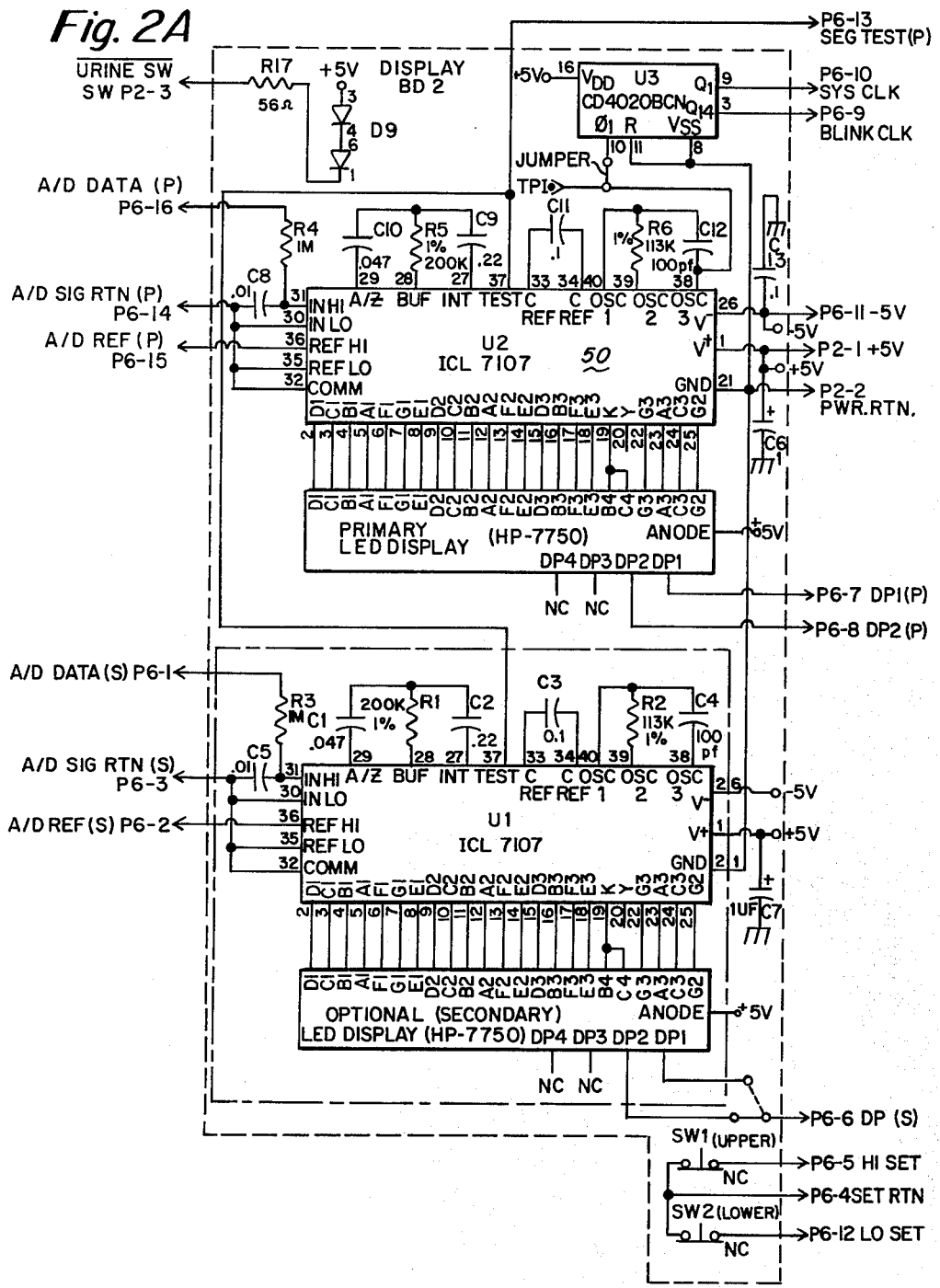
Figure 2C:
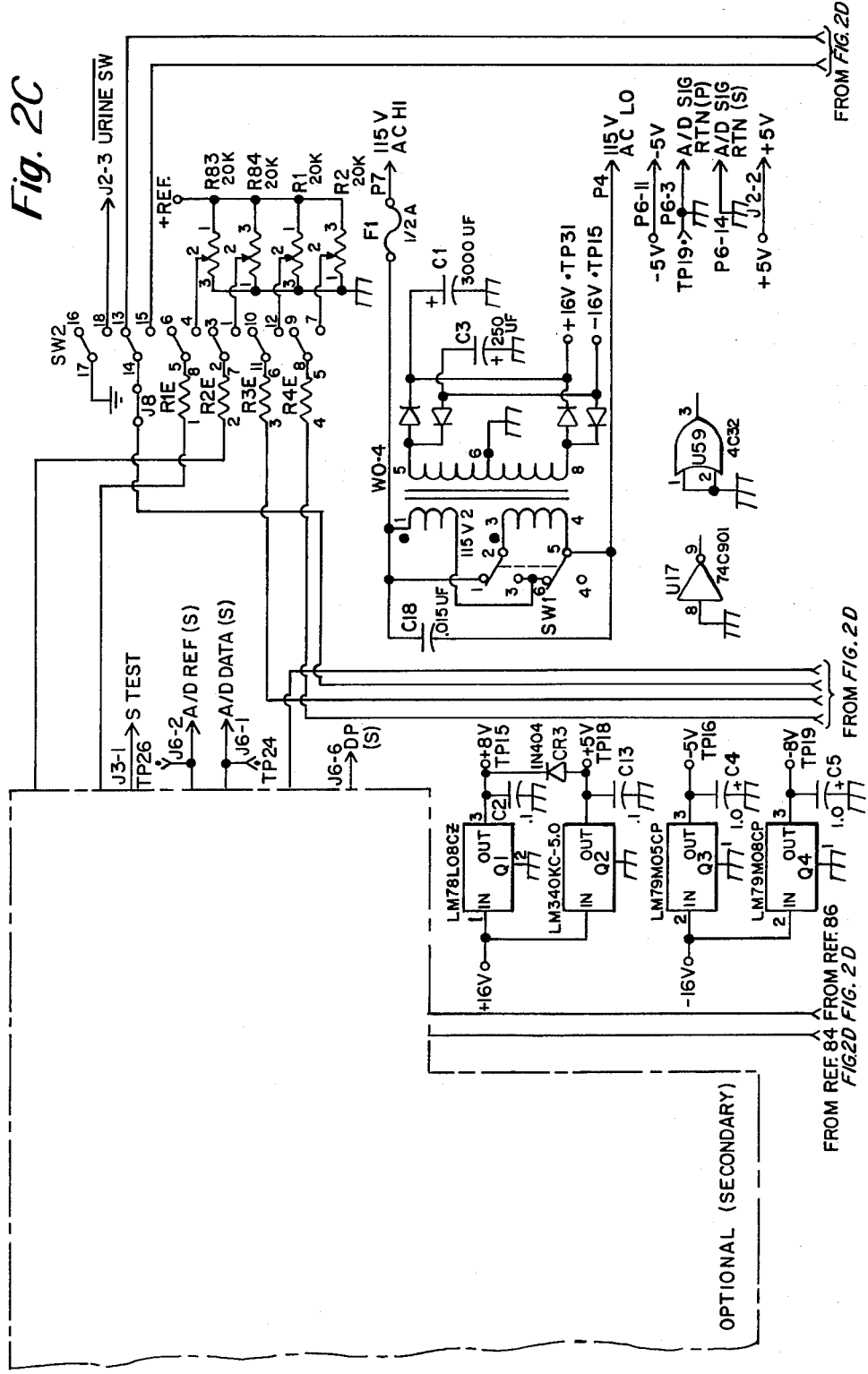
Figure 2D:
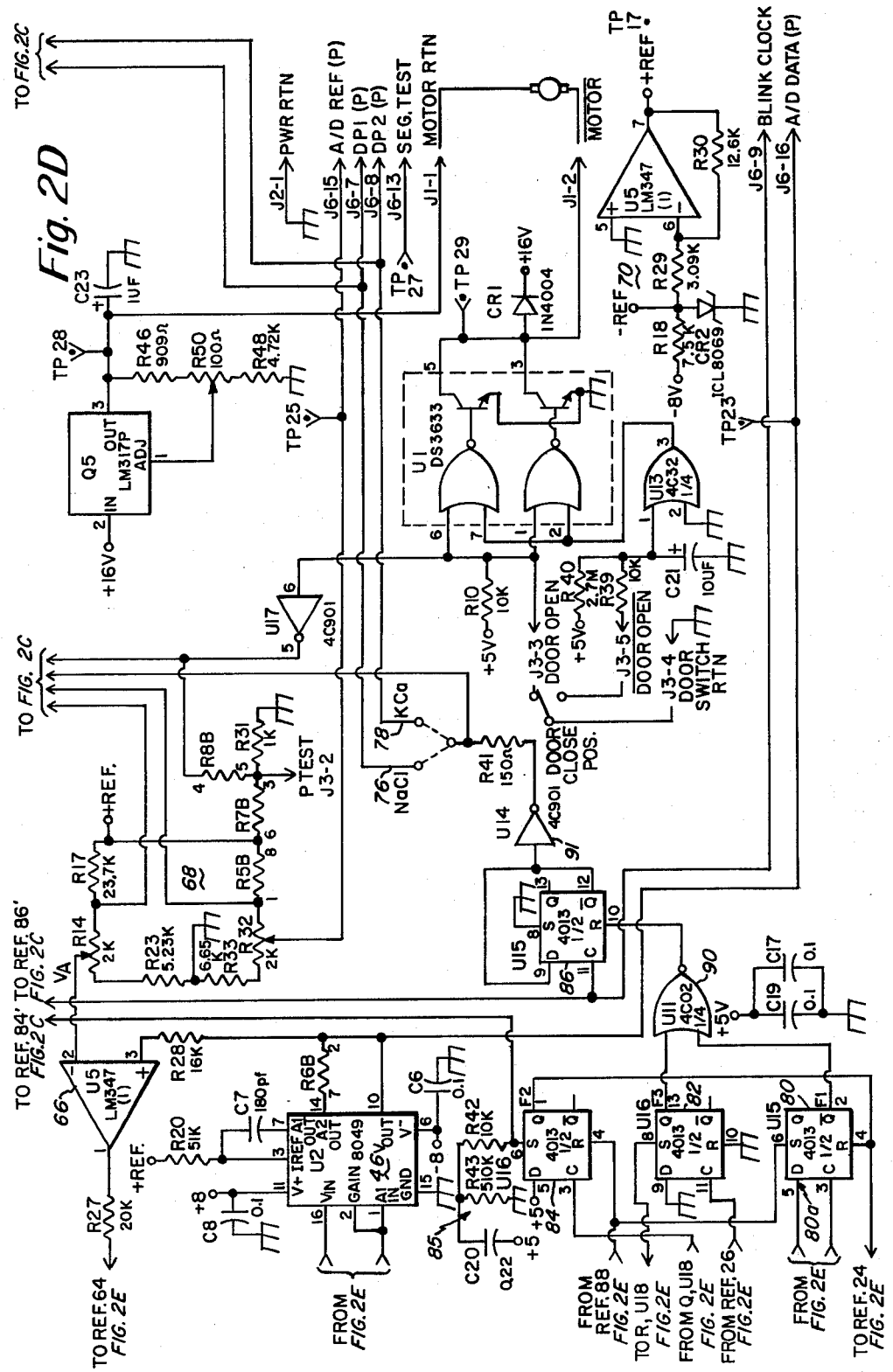
Figure 2E:
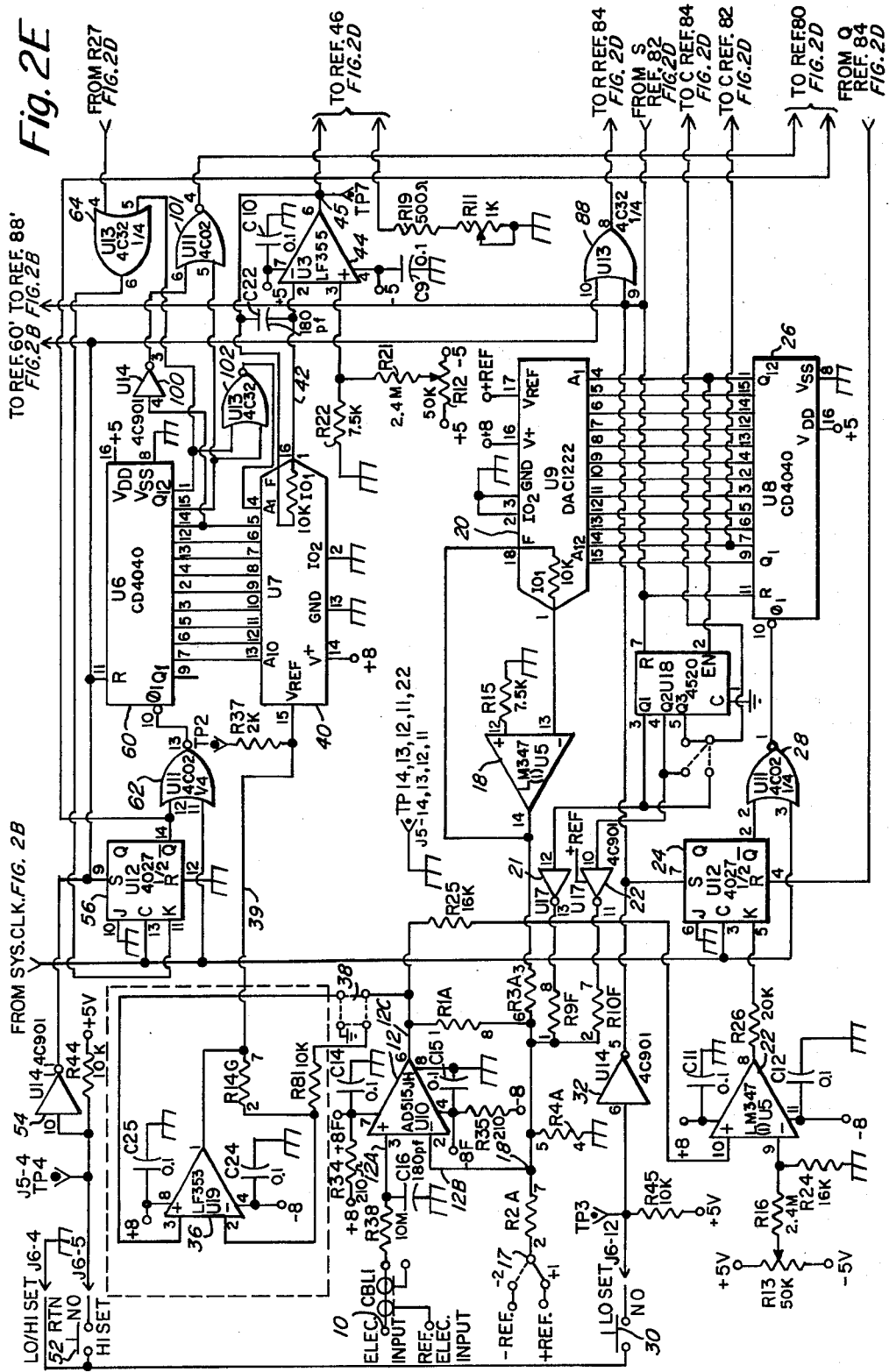

FIG. 1 is a block diagram showing the principle components of the circuit system of the present invention.

The details of the entire system are shown in FIGS. 2A–2E. Like reference characters will be used through the drawings to identify like components.

The electrode input is at terminal 10 and couples to buffer 12 which may be of an operational amplifier type having a signal input 12A, a reference input 12B, and an output 12C. Associated with the buffer 12 is a bias network 14 which comprises resistors R1A, R3A, R9F, and R10F. A reference bias input at terminal 17 is coupled to buffer 12 at input 12B via resistor R2A. Buffer 12 input 12B, couples by way of resistor R3A to the amplifier 18 which couples from the output of the digital-to-analog converter (DAC) 20. Further bias is suplied to the input 12B by resistors R9F and R10F operating in unison with inverters 19 as a digital-to-analog converter extension to converter 20.

The low standard circuit also includes comparator 22, flip-flop 24, counter 26, counter extension 27, and gate 28. The low standard set switch 30 has one side grounded and its other side coupled by way of inverter 32 to the set input of the flip-flop 24 and also to the reset input of the counter 26 and its extension 27. There is also provided an inverter 36 and associated jumper 38. The jumper 38 can be moved to alternate positions to either include inversion or not of the signal from the output 12C of the buffer 12. The output from the jumper 38 couples by way of line 39 to the multiplying digital-to-analog converter 40. The output from the converter 40 couples by way of line 42 to the device 44, with the output from the device 44 at node 45 coupling to the device 46. The device 44 may be of a type operational amplifier having one input coupled to a reference. The device 46 is an anti-logarithmic device for taking into account the logarithmic relationship between electrode voltage and concentration. The output from the device 46 couples to the digital panel meter 50.

The high standard circuit includes the high set switch 52 which has one side grounded and the other side coupled by way of inverter 54 to both the set input of the flip-flop 56 and the reset input of the counter 60. There is provided a gate 62 between the flip-flop 56 and the counter 60. The gate 62 also receives the clock input. Similarly, the gate 28 discussed previously in connection with the low standard circuit also receives a clock input. The clock signals are used for counting the counter 26 with its extension 27 and the counter 60. The resetting of the flip-flop 56 is from the output of gate 64. There is also provided feedback from the output of device 46 to one input of comparator 66. The other input to the comparator 66 is a voltage shown on line 67 derived from a voltage reference circuit 68. The output of the comparator device 66 couples by way of the gate 64 to cause the resetting of flip-flop 66 to terminate the counting of counter 60. Counter 60 may similarly be terminated by a fail condition also by way of the gate 64.

Preparing the apparatus to perform the desired test calls for the operator to fill the proper sample chambers and calibrate the apparatus. One of these sample chambers receives the low standard solution and the other receives the high standard solution. The fluids may be placed in the sample chambers with the use of a hypodermic filled with the proper fluid. As far as the mechanical operation is concerned, reference is made to the copending application. The electrode receptacle and electrodes are placed over the sample cup containing the 300 microliters of low standard solution. The operator immerses the sensing portion of the electrodes into the standard solution and at the same time the oscillating table is operated thereby agitating the standard solution. Within approximately 20 seconds the oscillations cease and about 10 seconds later, the digital readout display becomes stable. The low standard set switch 30 is then depressed and the reading is noted. Then the electrode is moved to the sample cup containing the high standard solution. The test procedure is then repeated as hereinbefore described except that the switch 52 for the high standard fluid is depressed.

The bias for the buffer device 12 is supplied by way of resistor R2A at the terminal 17. This signal is provided from the reference circuit 70 shown in FIG. 2D which provides positive or negative reference signals to the terminal 17 depending upon the specific electrode characteristics. When the low standard switch 30 is depressed, this initiates counting of the counter 26 and its extension 27, from a zero count and starts it counting up under control of the flip-flop 24 which is set concurrently with the resetting to zero of the counter 26 and its extension 27. The counting of counter 26 along with its extension 27, ceases when there is a comparison by the comparator 22 when the output 12C from the device 12 is at zero or also when a failure occurs due to too high a counting of the counter 26 and its associated extension 27. The digital value at the output of the counter 26 is fed to the digital-to-analog converter 20 for providing an output analog signal by way of the device 18 to the resistor R3A for essentially providing a setting of the offset adjustment for the buffer device 12. Similarly, the counter extension 27 is fed to the digital-to-analog converter extension 19, comprised of inverters 21 and 22 and resistors R9F and R10F essentially providing an additional offset adjustment for the buffer device 12. This causes the input to the multiplying digital-to-analog converter 40 to be zero at any electrode input within the electrode bias range. Pressing the low standard set switch 30 clears any previous failure. Thus, for the low standard operation the digital meter is essentially forced to read the low standard value by this feedback adjustment of its offset reference voltage from the output of the converter 20 and the converter extension 19, assuming the electrode voltage is within range.

After the low standard calibration has been effected, then the high standard set switch 52 may be operated. The closure of switch 52 is coupled by way of inverter 54 to set the flip-flop 56 and at the same time reset the counter 60 to a zero count. The combination of the setting of the flip-flop and the resetting of the counter causes the counter to start counting up from this initial zero setting. The converter 40 is a multiplying digital-to-analog converter as previously mentioned. Thus, the analog input to the converter 40 is essentially multiplied by the digital input from the counter 60. The converter 40 multiplies any change in electrode input since the last low standard set operation by the value of the counter 60. This counting operation is normally terminated by a signal from comparator 66 at its output. It is noted the comparator 66 receives the output voltage from the device 46 and also a preset voltage on line 67 from the network 68. The voltage 67 is adjusted to force the digital panel meter to read the high standard value associated with the high sample. Thus, when the output of the device 46 matches the voltage on line 67, then the counting of counter 60 ceases. There is also an interruption of counting upon failure. For example, this will occur when the output of counter 60 is too high. This is controlled by way of the gate 64.

After the low and high standard settings have been properly made, the offset correction is essentially stored in the counter 26 and its extension 27 while the gain correction is stored in the counter 60. If these values are of a proper magnitude, the electrode input values cause proper concentrations to appear on the digital readout. The device 46 takes into account the logarithmic relationship between electrode voltage and concentration to assure proper interpolation and extrapolation around the low and high standard values and the fluid being tested.

There is also shown in FIG. 2 a number of flip-flops which are used to determine certain failure conditions. Failed calibration occurs basically in four ways and causes the decimal point to blink by way of signals on either lines 76 or 78. The failed calibration circuitry includes flip-flops 80, 82, 84 and 86 and gates 88, 65 and 90 and inverter 100. The low standard set switch 30 sets flip-flop 82. This flip-flop is cleared by a count from the counter 26. This failure indication assures that the output from buffer 12 is not at too high a value to start with. This is a count-too-low failure. The output from the flip-flop 82 couples by way of gate 90 to the reset of flip-flop 86. It is noted that the negation output from the flip-flop 86 couples by way of inverter 91 to either of the lines 76 or 78.

A second failure is detected by flip-flop 84 and this occurs when the output terminal of counter extension 27 flips to its "one" state indicating a count-too-high failure. The indication from flip-flop 84 at its assertion output occurs at power-up to the set input to the flip-flop from the network 85.

Failure F1, indicated by flip-flop 80 is established by sensing the count of counter 60 at the end of the counting sequence when the flip-flop 56 is reset. A failure is indicated if counter 60 does not stop between one-quarter and one-eighth full count. This condition is detected by inverter 100 and gate 65 and relayed to flip-flop 80 on its input 80A. Counter 60 above one-quarter full count represents electrode slopes that are too low and below one-eighth full count represents electrode slopes that are too high. The multiplying digital-to-analog converter 40 allows slope calibration for counter 60 between essentially zero and one-half scale but the failure indicates a marginal electrode for any range other than one-eighth to one-quarter full count.

Gate 102 forces a half scale or above slope into converter 40 should counter 60 terminate above half scale so that the instrument does not appear "dead" since converter 40 is not tied to the most significant bit of the counter 60.

There is also included in FIG. 2 details of other portions of the electronics associated with the testing apparatus. This includes certain door switching circuitry and motor controls. The details of this portion of the circuitry are not discussed in detail as they pertain more to the subject matter of the copending application.

Having described one embodiment of the present invention, it should now become apparent to those skilled in the art that numerous other embodiments are contemplated as falling within the scope of this invention.

What is claimed is:

1. Electronic circuit for measuring and displaying ion concentration comprising;

an input terminal for receiving an electrical input signal from an electrode representative of ion concentration, calibrating means including low standard circuit means for calibrating said electronic circuit with a low standard sample and including a low standard set switch adapted for initial operation by the operator, first digital storage means responsive to said set switch for storing a signal value representative of offset correction to thus modify said input signal, and buffer means responsive to said offset correction signal and the electrode input signal for establishing a low standard signal, and high standard circuit means for calibrating the electronic circuit with a high standard sample and including a high standard set switch adapted for operation by the operator, second digital storage means responsive to said high standard set switch for developing a signal representative of gain correction, and means receiving said low standard signal and responsive to the gain correction signal to modify said low standard signal from the buffer means to provide a normalized electrode signal, and means responsive to said normalized electrode signal to provide an ion concentration reading from such electrode input signal and display said ion concentration.

2. Electronic circuit as set forth in claim 1 wherein said first digital storage means of said low standard circuit includes a counter responsive to operation of said low standard switch to start counting and responsive to an electrode signal from said input terminal to stop counting at a predetermined value.

3. Electronic circuit as set forth in claim 2 wherein the low standard circuit includes a bias circuit controlling the output of said buffer means, said bias circuit including a digital to analog converter whose input is from said first storage means and whose output is connected to an input of said buffer means.

4. Electronic circuit as set forth in claim 3 wherein the buffer means includes a first input from said electrode and a second input from a reference bias circuit representing the electrical characteristics of the electrode.

5. Electronic circuit as set forth in claim 1 wherein the low standard signal modifying means includes a counter connected to the high standard switch and having an output connected to a multiplying digital-to-analog converter having a digital input from said high standard circuit means and responsive there to modify the analog input from said low standard means.

6. Electronic circuit as set forth in claim 5 including a comparator in said high standard circuit responsive to the value in said second digital storage means and a fixed high standard sample voltage value to compare said value to define gain normalization.

7. Electronic circuit as set forth in claim 1 wherein said display means includes a digital readout display for displaying concentration directly.

8. Electronic circuit as set forth in claim 1 wherein each of said low standard circuit and high standard circuit includes means connected to counters in said high and low standard circuits to compare the values in said counters to predetermined values to detect calibration failure.

* * * * *